United States Patent [19]

Schneider

[11] Patent Number: 4,752,474

[45] Date of Patent: Jun. 21, 1988

[54] LIVE RABIES VACCINE

[76] Inventor: Lothar G. Schneider, P.O. Box 80 03 20, D-6230 Frankfurt am Main 80, Fed. Rep. of Germany

[21] Appl. No.: 888,723

[22] Filed: Jul. 24, 1986

[30] Foreign Application Priority Data

Jul. 26, 1985 [DE] Fed. Rep. of Germany ....... 3526809

[51] Int. Cl.$^4$ ............................................. A61K 39/205
[52] U.S. Cl. ..................................... 424/89; 435/235; 435/237
[58] Field of Search ................... 424/89; 435/235, 237

[56] References Cited

U.S. PATENT DOCUMENTS

| | | | |
|---|---|---|---|
| 4,014,991 | 3/1977 | Baer et al. | 424/89 |
| 4,169,761 | 10/1979 | Precausta et al. | 435/235 |
| 4,196,265 | 4/1980 | Koprowski et al. | 424/86 |
| 4,320,115 | 3/1982 | Bijlenga | 424/89 |
| 4,347,239 | 8/1982 | Bass et al. | 424/89 |
| 4,400,472 | 8/1983 | Bijlenga | 435/237 |
| 4,429,045 | 1/1984 | Bass et al. | 435/237 |
| 4,584,194 | 4/1986 | Bass et al. | 435/237 |
| 4,650,673 | 3/1987 | Johnston et al. | 424/84 |

OTHER PUBLICATIONS

Abelseth, Can. Vet. Jour., 5: 279-286 (1964).
Baer et al., American Journal of Epidemiology, 93: 487-490 (1971).
Tierarztl. Umschau, 37: 165-176 (1982).
Hafliger et al., Zbl. Vet. Med. B, 29: 604-618 (1982).
Sato et al., Archives of Virology, 53: 269-273 (1977).
Steck, et al., Zbl. Vet. Med. B, 29:372-396 (1982).
von Schneider, et al., Tierarztl. Umschau, 38: 476-480 (1983).
Schneider, L. G., Tagung der Fachgruppe Tierseuchenrecht Deutsche Veterinarmedizinische Gesellschaft, 14/15 Jun., 1984, pp. 25-55, 1-7, 8-24, 56-58.
Wandeler, et al., Comp. Immun. Microbiol. Infect. Dis. 5: 173-176 (1982).

*Primary Examiner*—Shep K. Rose

[57] ABSTRACT

A process for the preparation of a live rabies vaccine for the oral vaccination of Canidae is described.

Special variants of the SAD rabies virus strain, called variant strain $VA_1$, $VA_{12}$, $VA_{17}$ and $VA_{20}$, are propagated in the BSR-19 cell line and processed in a known manner to give a vaccine which is effective on oral administration to foxes and dogs.

4 Claims, No Drawings

LIVE RABIES VACCINE

The present invention relates to a Street Alabama Dufferin (SAD) variant vaccine for animals against rabies, which contains live attenuated virus. The vaccine can be administered parenterally or orally.

Live vaccines for the immunization of animals have already been disclosed. They are normally administered parenterally. The disadvantage of all live vaccines is their low stability in the liquid form. For this reason live vaccines are usually freeze-dried, have to be stored in the cold to comply with directions, and have to be used without delay after reconstitution. These live vaccines are guaranteed to be innocuous and efficacious only on intramuscular administration. Cases of postvaccinal rabies have been observed occasionally with other modes of administration, especially subcutaneous injection, and regularly with intracerebral (i.c.) injection.

It has emerged that inoculation of domestic animals cannot reach the reservoir of rabies—especially wild living carnivores. Hence there is a permanent source of infection of non-immunized animals and humans.

The ERA vaccine described in Can. Vet. Jour. 5, 279–286, 1964, has been adapted to $BHK_{21}$ cells (Am. J. Epidemiol. 93, 487–490, 1971; $ERA/BHK_{21}$) and has proved to be immunogenic and innocuous in foxes when drops of the liquid vaccine were placed on the tongue. However, the $ERA/BHK_{21}$ virus was still pathogenic for cotton rats and muskrats.

Although the Flury HEP virus, clone 675 (Tierärztl. Umschau 37, 165–176, 1982) proved to be substantially apathogenic for a number of small wild living mammals, it showed a tendency for latent presence, since it was still detectable in the brain of many animals after 100 days. Furthermore, it is not genetically stable and its immunogenicity in foxes is low, since even relatively high virus doses do not consistently result in successful immunization.

In Switzerland successful immunization of foxes has to date been achieved most reliably with the SAD virus, the attenutated virus strain which is also present in the ERA vaccine (Häfliger et al., Zbl. Vet. Med. B, 29, 604–618, 1982).

However, a crucial disadvantage of the Swiss SAD vaccin is its low stability, which can result in considerable losses of efficacy. Single doses cannot be stored frozen, and the vaccine has to be made available in the field not later than the day following bottling. The effects of temperature result in the virus titer falling after about 3 days to below the dose effective in foxes.

Thus the object of the invention was to develop a vaccine for controlling rabies in animals, which can be administered orally, which does not have the disadvantages mentioned, which on oral administration is immunogenic, innocuous for animals, genetically stable, clearly defined and distinguishable from wild strains by markers, and which is stable for the longest possible time on exposure to changing temperatures.

Surprisingly, this object has been achieved in the following manner: the virus strain $SAD/BHK_{21}$ (Häfliger et al., see above) was propagated on a number of cell clones of BSR cells (Sato, M. et al., Archives Virology 53, 269–273, 1977) and the relevant virus yields were determined. The BSR-19 cell clone (Sato, M. et al., loc. cit.) was selected by cloning on soft agar. A variant virus which was obtained in this way and had a constant virus titer of $1-2 \times 10^8$ TCID50/ml was selected, called SAD Variant $VA_1$ and deposited under No. I-430 at the Collection Nationale de Cultures de Microorganismes (C.N.C.M.), 25 rue du Docteur Roux, 75724 Paris Cedex 15. Selection was based on a high virus yield and substantial apathogenicity for mice. The virus was stored freeze-dried. The cells of the clone BSR-19 were stored in liquid nitrogen.

The variant strain $SAD/VA_1$ shows less pathogenicity than the vaccine strain $ERA/BHK_{21}$ and higher stability and greater efficacy than the vaccine strain $SAD/BHK_{21}$.

Starting from variant strain $SAD/VA_1$ and using the monoclonal antibody MW-187.2.8 the variant strains $SAD/VA_{12}$ (C.N.C.M. No. I-431) and $SAD/VA_{17}$ (C.N.C.M. No. I-432) were obtained by passages in BSR cells. Starting from varian strain $SAD/VA_{12}$ and using the monoclonal antibody PM 13, another variant strain $SAD/VA_{20}$ was obtained. The virus strains $SAD/VA_1$, $VA_{12}$, $VA_{17}$, $VA_{20}$ are further referred to as variant strains. The neutralization pattern of the variant strains $VA_{12}$, $VA_{17}$ and $VA_{20}$ towards a number of defined monoclonal antibodies is shown in Tab. 1.

TABLE 1

| Virus | Monoclonal antibodies | | | | | |
|---|---|---|---|---|---|---|
| | MW187.2.8 | E529 | C37.12.4 | C231/A | PM13 | PM37 |
| SAD/starter | 8000[1] | 40000 | 50 | 50 | 0 | 50 |
| $SAD/VA_1$ | 8000 | 300 | 40000 | 1500 | 0 | 25 |
| $SAD/VA_{12}$ | 0 | 0 | 0 | 1500 | 0 | 25 |
| $SAD/VA_{17}$ | 0 | 300 | 0 | 3000 | 0 | 50 |
| $SAD/VA_{20}$ | 0 | 200 | 300 | 0 | 25 | 0 |

[1]reciprocal antibody titer in the neutralization assay

Hence the invention relates to a live vaccine for the immunization of animals against rabies, which contains a SAD variant virus whose activity is maintained in the liquid form after at least three days at not below 20° C.

The invention particularly relates to a live vaccine which contains one of the SAD variant strains $VA_1$, $VA_{12}$, $VA_{17}$ or $VA_{20}$.

The invention also relates to a process for the preparation of a live vaccine of this type, which comprises use of the monoclonal antibody MW 187.2.8 and, where appropriate, PM 13 to isolate from the SAD virus population one of the variant strains SAD/$VA_1$, SAD/$VA_{12}$, SAD/$VA_{17}$ or SAD/$VA_{20}$, and comprises the addition of auxiliaries, additives and/or stabilizers which are customary for the preparation of vaccines using a suspension of one variant of above type, and, where appropriate, freeze-drying.

The invention particularly relates to a process for the preparation of a live vaccine of this type, which comprises the addition of auxiliaries, additives and/or stabilizers which are customary for the preparation of vaccines using a suspension of one of the variant strains SAD/$VA_1$, SAD/$VA_{12}$, SAD/$VA_{17}$ or SAD/$VA_{20}$ and, where appropriate, freeze-drying.

A vaccine of this type can be prepared by known methods by use of, for example, the BHK-BSR cell line and one of the variant strains $VA_1$, $VA_{12}$, $VA_{17}$ or $VA_{20}$ described in the specification. The cells of the BHK-BSR cell line for this purpose can be propagated in monolayer cell cultures in several steps with a split rate of 1:2 to 1:15, preferably 1:3 to 1:10. The cell cultures are propagated with a predefined virus concentration and by use of the cell-mixing technique, for example by use of 50 g/ml DEAE-dextran, which is removed again from the cell culture by a centrifugation process. The viruses are harvested at 2-5 day intervals by aspiration of the virus containing nutrient medium. The harvested viruses are stored at $-20°$ C. to $-80°$ C. for subsequent use. For oral application the virus suspension is used to adjust the final vaccine to a virus concentration of, preferably, $3-4\times10^7 TCID_{50}$ (tissue culture infectious doses) per vaccination dose (1.8 ml) by use of a buffer, for example a 0.1M NaCl/phosphate buffer solution of pH 7.2 which contains bovine serum albumin, preferably 0.3 mol/l, and egg yolk, preferably 100 g/l, as stabilizers, the vaccine being dispensed into, preferably, blister packs composed of a PVC dimple film and a thermally coated aluminum covering foil. The finished vaccine is stored deep-frozen, for example at $-20°$ C. to $-35°$ C.

$VA_{12}$, $VA_{17}$ and $VA_{20}$ variant strains were tested for their pathogenicity on intracerebral, intramuscular and oral administration in dilution from 1 to $10^{-5}$ to adult mice. None of the 20 infected mice in each group showed symptoms of rabies infection.

The variant strains $VA_1$, $VA_{12}$, $VA_{17}$ and $VA_{20}$ were propagated by one more passage in BSR-19 cells and were processed in a known manner (Häfliger et al., 1982) to give a vaccine which can be administered orally. The vaccines were then packed in a bait which was offered to foxes for oral intake.

When the vaccine concentration was $10^5$ TCID50 or higher, all the foxes which had received the vaccine formed antibody titers in the protective range from 1:65 to 1:1300.

All the immunized foxes proved to be immune between 3 and 13 months after administration. No side effects of a systemic or local nature were observed.

When used in the field, preferable an antigen concentration of $2\times10^7$ TCID50/ml is used. In a controlled field trial (area about 400 km²), of 25 foxes which were killed in the vaccination area within 6 months after the vaccination (=laying out of the baits containing the vaccine) 20 foxes (=80%) had rabies antibodies with a mean antibody titer of 1:492 (1:60 to 1:1620).

In order to test the actual protection of the orally immunized foxes against an infection with highly pathogenic wild-type virus, 18 foxes were immunized orally with baits containing the variant strain $SAD/VA_{12}$ in two virus concentrations, and were subjected to a challenge with pathogenic wild virus 3 months after the vaccination. In parallel 24 foxes were immunized in the same way with $SAD/BHK_{21}$ vaccine according to the state of the art, in three virus concentrations, and subjected to challenge. A third vaccine originating in France, which was apathogenic for adult mice in the same way as $SAD/VA_{12}$, was tested on a further 18 foxes.

Whereas all 18 of the foxes immunized with the vaccine according to the invention survived, only 42% of the 24 immunized with $SAD/BHK_{21}$ vaccine and none of the 18 animals treated with the third vaccine survived, whereas 5/5 non-vaccinated foxes used as challenge control died of rabies.

Furthermore, 13 foxes were immunized orally with baits containing the variant strain $SAD/VA_1$ ($2\times10^7$ IU/mL) and subjected to challenge with highly pathogenic wild-type virus 1 year after vaccination. All 13 foxes survived the challenge, whereas 5 non-vaccinated foxes contracted rabies.

This shows that foxes are protected against infection with the rabies virus for at least 1 year after oral immunization with SAD variant strains.

Furthermore, the variant strains $VA_1$ and $VA_{12}$ were administered orally in baits to a total of 16 dogs which were at least 1 year old (virus dose: $2\times10^7$ to $2\times10^9$). 3-4 weeks after the vaccination, all dogs had antibodies against rabies in the protective range.

This result is surprising because it has not been possible by administration of conventional vaccines to orally immunize dogs with adequate reliability.

It has not been disclosed earlier that an adequate protection from rabies can be conferred to dogs by oral intake of baits containing variant SAD vaccine viruses. For the first time this opens the possibility of immunizing dogs against rabies in areas where they are uncontrollable in a way similar to wild animals in Germany.

The variant strain $SAD/VA_1$ was administered orally to adult mice in various concentrations, and the mortality rate was compared with the $ERA/BHK_{21}$ vaccine strain. The residual pathogenicity found for $SAD/VA_1$ variant strain was 4.5%, and that found for $ERA/BHK_{21}$ virus strain was 35%.

Furthermore, the variant strain $SAD/VA_1$ was administered orally in various concentrations to adult muskrats. None of the 22 inoculated muskrats contracted rabies. In the observation period lasting up to 106 days after injection, $SAD/VA_1$ variant strain was not detectable either in the infectious state or as virus antigen. In contrast, $ERA/BHK_{21}$ virus was still pathogenic in 61 of 95 muskrats.

Furthermore, the variant strain $SAD/VA_1$ was stored at 4° C., 22° C. and 37° C., and the virus titer was determined each day. Compared with the vaccine strain $SAD/BHK_{21}$ of the state of the art, the proportional inactivation of the variant strain $SAD/VA_1$ was markedly less at all temperatures tested, for example almost 2 $\log_{10}$ steps, which means about 99%, at 37° C.

When the variant strain $SAD/VA_1$ ($5\times10^{-7}$ IU/ml) was stored under field conditions for up to 25 days and the virus content was determined by titration at intervals of one or more days, no reduction in the virus titer below $10^6$ TCID50/ml was observed even at daily temperatures around 40° C. (20° C. at night). Samples which had been stored in the field for 14 days were administered orally to 8 foxes. All the foxes had detectable antibodies against rabies in the range 1:250 to 1:6200 after 21 days.

Vaccine dispensed in single doses was stored at $-20°$ C. for up to 6 months without any detectable loss of titer. In contrast, the strain $SAD/BHK_{21}$ of the state of the art cannot be stored deep-frozen after dispensing in single doses but must be immediately laid out in the field in order to avoid losses of titer.

EXAMPLE 1

Isolation of the variant strains $VA_{12}$ and $VA_{17}$

A suspension of the variant strain $SAD/VA_1$ was diluted 1:10, mixed with equal parts by volume of a solution of the monoclonal antibody (MAb) M187.2.8, and the mixture was incubated at 37° C. for 90 min. The virus/antibody mixture was then distributed to about 50 plaque dishes and incubated at 35° C. for 5 days. The virus plaques were selected, subjected to another passage, and their neutralization behavior towards the selective and other MAb was tested. At the same time, the residual pathogenicity was examined by i.c., i.m and oral administration to adult mice.

The neutralization pattern of the variant strains $VA_{12}$ and $VA_{17}$ is shown in Table 1, and the pathogenicity of the SAD variant strains $VA_{12}$ and $VA_{17}$ in adult mice is described above. No cases of illness or death were observed even after intracerebral administration of the variant strains.

However, the variant strains $VA_{12}$ and $VA_{17}$ were still pathogenic for suckling mice on i.c. administration. When brain material from the suckling mice inoculated with variant strain $VA_{12}$ was administered i.c. to adult mice, the latter contracted rabies. In contrast to the variant strain $VA_{12}$, i.c. inoculation of brain material from suckling mice inoculated with variant strain $VA_{17}$ did not result in contraction of rabies by adult mice, even after several passages in suckling mice.

EXAMPLE 2

Isolation of the variant strain $VA_{20}$

A suspension of the SAD variant strain $VA_{12}$ selected by monoclonal antibody (Example 1) was mixed with an equal part by volume of a solution of the monoclonal antibody PM 37, and the mixture was incubated at 37° C. for 90 min. The virus/antibody mixture was then distributed over plaque dishes and incubated at 35° C. for 5 days. The virus plaques which formed were selected and examined as described in Example 1.

The neutralization behavior of the variant strain $VA_{20}$ is shown in Table 1. Its pathogenic properties in adult mice are described above. The variant strain $VA_{20}$ was still pathogenic for suckling mice on i.c. administration. Brain material from the suckling mice inoculated with variant strain $Va_{20}$ did not result on i.c. inoculation, in contraction of rabies by adult mice, even after several passages in suckling mice.

The advantage of variant strains $VA_{20}$ over $VA_{12}$ and $VA_{17}$ is the stability of the non-pathogenic properties, which was achieved by multiple selection using monoclonal antibodies.

EXAMPLE 3

The vaccine is prepared in accordance with the known regulations, for example the requirements of the WHO and the requirements of the European Pharmacopoeia. As a rule, the dosage is between 0.5 and 2 ml, but may also comprise other volumes. The important point here is to adhere to the active substance as indicated.

For this purpose, 3 ampules containing BSR-12 cell material which had been stored at $-180°$ C. were thawed, suspended in a mixture of ME Medium (ME Medium=Minimal Essential Medium; supplied by Serva, Heidelberg, FRG; cat. no. 47294) and 100 ml of calf serum per liter of ME Medium, and distributed into 3 Roux bottles. After 3 days, the BSR-12 cells were removed by trypsinization, suspended in sufficient ME Medium and distributed into 15 Roux bottles. After 4 days, the cells were again removed by trypsinization, suspended in Eagle's Medium (Glasgow modification) with the addition of 50 g of DEAE-dextran and SAD/-$VA_1$ virus, dilution $10^{-3.6}$, stirred at $+37°$ C. for 30 min, centrifuged, suspendet in 4000 ml of ME Medium $+10\%$ calf serum, and distributed into 50 Roux dishes. After a further 3 days, the cell-growth medium was replaced by a maintenance medium (Eagle's medium/-Glasgow modification) which contained 3 ml/l bovine serum albumin.

After 2 days 4000 ml of antigen suspension, virus titer $2 \times 10^8/TCID50$ ml (titration in BHK-cell cultures), and after a further 2 days another 4000 ml, virus titer $2 \times 10^8$ TCID50/ml, were obtained.

These suspensions were adjusted to a virus concentration of $3-4 \times 10^7$ $CID_{50}$ (Tissue culture infectious doses) per vaccination dose (1.8 ml) using a 0.1 molar sodium chloride/phosphate buffer solution of pH 7.2 which contained 0.3 ml/l bovine serum albumin and 100 g/l egg yolk as stabilizers, and dispensed into blister packs composed of a PVC dimple film and a thermally coated aluminum covering foil. The finished vaccine was stored deep-frozen at $-20°$ C. to $-35°$ C.

I claim:

1. A live vaccine for the immunization of animals against rabies, which contains an acceptable carrier and an effective dosage amount of SAD variant strain VA, $VA_{12}$, or $VA_{17}$ a SAD variant virus whose activity is maintained in the liquid form after at least 3 days at not below 20° C.

2. A live vaccine as claimed in claim 1, wherein the variant virus remains apathogenic for adult mice after intracerebral passage in suckling mice.

3. A process for the preparation of a live vaccine as claimed in claim 1, which comprises the addition of auxiliaries, additives and stabilizers which are customary for the preparation of vaccines to a suspension of one of the variant strains SAD/$VA_1$, SAD/$VA_{12}$, or SAD/$VA_{17}$.

4. The process of claim 3 comprising the additional step of freeze-drying said vaccine.

* * * * *